United States Patent [19]

United States Patent [19]
Seidel

[11] Patent Number: 5,892,074
[45] Date of Patent: Apr. 6, 1999

[54] SYNTHESIS OF CONJUGATED LINOLEIC ACID (CLA)

[76] Inventor: Michael C. Seidel, 61 Hickory La., Chalfont, Pa. 18914

[21] Appl. No.: 800,567

[22] Filed: Feb. 18, 1997

[51] Int. Cl.$^6$ .................................................. C07C 51/347
[52] U.S. Cl. .......................................... 554/126; 554/154
[58] Field of Search ...................................... 554/154, 126

[56] References Cited

U.S. PATENT DOCUMENTS 5,554,646   9/1996   Cook et al. ............................. 514/560

OTHER PUBLICATIONS

"Conjugated linoleic acid offers research promise," *Inform*, vol. 7, No. 2 (Feb. 1996) pp. 152, 153, 156–159.
K.N. Lee et al, "Conjugated linoleic acid and atherosclerosis in rabbits," *Atherosclerosis* 108 (1994) pp. 19–25.
C. Ip et al., "Conjugated Linoleic Acid Suppresses Mammary Carcinogenesis and Proliferative Activity of the Mammary Gland in the Rat," *Cancer Research* 54 (Mar. 1, 1994) pp. 1212–1215.
C. Ip et al., "Mammary Cancer Prevention by Conjugated Dieonic Derivative of Linoleic Acid," *Cancer Research* 51 (Nov. 15, 1991) pp. 6118–6123.
Y. L. Ha et al., "Inhibition of Benzo(a)pyrene–induced Mouse Forestomach Neoplasia by Conjugated Dieonic Derivatives of Linoleic Acid," *Cancer Research* 50 (Feb. 15, 1990) pp. 1097–1101.
Berdeaux et al, "Large–Scale Synthesis of Methyl cis–9, trans–11–Octadecadienoate from Methyl Ricinoleate," *JAOCS*, vol. 74, No. 8, pp. 1011–1015 (1997).
Gunstone et al, "Fatty Acids, Part 29 Methyl 12–Mesyloxyoleate as a Source of Cyclopropane Esters and of Conjugated Octadecadienotes," *Chem. Phys. Lipids*, 6, 147, pp. 121–134 (1971).

*Primary Examiner*—Paul J. Killos
*Assistant Examiner*—Deborah D Carr
*Attorney, Agent, or Firm*—Douglas G. Glantz

[57] ABSTRACT

A synthesis process for producing 9-cis, 11-trans octadecadienoic acid at room temperature in high yield is disclosed, including providing a tosylate or mesylate of a methyl ester of ricinoleic acid and 9-cis, 11-trans octadecadienoic acid formed when the tosylate or mesylate reacts with diazabicyclo-undecene. In one aspect, the tosylate of the methyl ester of ricinoleic acid is formed with tosyl chloride in a pyridine solvent. In one aspect, the mesylate of the methyl ester of ricinoleic acid is formed with mesyl chloride in acetonitrile and triethyl amine. In one aspect, the tosylate or mesylate is reacted with diazabicyclo-undecene in a polar, non-hydoxylic solvent of acetonitrile to form the preferred isomer of 9-cis, 11-trans octadecadienoic acid at room temperature in high yield.

20 Claims, 5 Drawing Sheets

SYNTHESIS OF CONJUGATED LINOLEIC ACID (CLA)

BACKGROUND OF THE INVENTION

1. Field of the Invention

This invention relates to novel synthesis of conjugated linoleic acid (CLA). In one aspect, this invention relates to novel synthesis of 9-cis, 11-trans octadecadienoic acid, also known as 9(Z),11(E)-octadecadienoic acid.

2. Background

Conjugated linoleic acid (CLA) is a general term used to name positional and geometric isomers of linoleic acid.

Linoleic acid is a straight chain carboxylic acid having double bonds between the ninth and tenth carbons and between the twelfth and thirteenth carbons. Linoleic acid is 9-cis, 12-cis octadecadienoic acid (9(Z),12(Z)-octadecadienoic acid). The numbers are counted from the carboxylic acid moiety. See Formula (1).

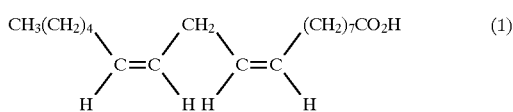 (1)

Conjugated linoleic acid (CLA) has two conjugated double bonds between the ninth and the twelfth carbons or between the tenth and thirteenth carbons, with possible cis and trans combinations. Conjugated double bonds means two or more double bonds which alternate in an unsaturated compound as in 1,3 butadiene. The hydrogen atoms are on the same side of the molecule in the case of cis. The hydrogen atoms are on the opposite side of the molecule in the case of trans. See Formula (2).

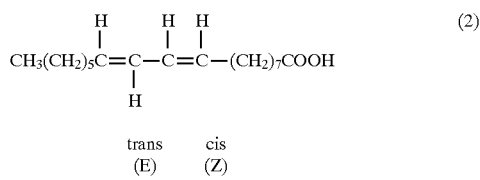

The free, naturally occurring conjugated linoleic acids (CLA) have been previously isolated from fried meats and described as anticarcinogens by Y. L Ha, N K. Grimm and M. W. Pariza, in Carcinogenesis, Vol. 8, No. 12, pp. 1881–1887 (1987). Since then, they have been found in some processed cheese products (Y. L. Ha, N. K. Grimm and M. W. Pariza, in J. Agric. Food Chem., Vol. 37, No. 1, pp. 75–81 (1987)).

Cook et al. U.S. Pat. No. 5,554,646 disclose animal feeds containing CLA, or its non-toxic derivatives, e.g., such as the sodium and potassium salts of CLA, as an additive in combination with conventional animal feeds or human foods. CLA makes for leaner animal mass.

INTRODUCTION TO THE INVENTION

The free acid forms of the CLA may be prepared by isomerizing linoleic acid. The terms "conjugated linoleic acids" and "CLA" as used herein are intended to include 9,11-octadecadienoic acid, 10,12-octadecadienoic acid, mixtures thereof, and the non-toxic salts of the acids. The non-toxic salts of the free acids may be made by reacting the free acids with a non-toxic base.

Historically, CLA was made by heating linoleic acid in the presence of a base. The term CLA (conjugated linoleic acid) refers to the prior art preparation involving alkali cooking of linoleic acid.

A conventional method of synthesizing CLA is described in Example I. However, CLA may also be prepared from linoleic acid by the action of a linoleic acid isomerase from a harmless microorganism, such as the Rumen bacterium *Butyrivibrio fibrisolvens*. Harmless microorganisms in the intestinal tracts of rats and other monogastric animals may also convert linoleic acid to CLA (S. F. Chin, J. M. Storkson, W. Liu, K. Albright and M. W. Pariza 1994, J. Nutr., 124; 694–701).

The prior art method of producing conjugated linoleic acids (CLA) can be seen in the following Example I using starting materials of linoleic acid or safflower oil.

EXAMPLE I

SYNTHESIS OF CONJUGATED LINOLEIC ACIDS (CLA) FROM LINOLEIC ACID/SAFFLOWER OIL

Ethylene glycol (1000 g) and 500 g potassium hydroxide (KOH) are put into a 4-neck round bottom flask (5000 ml). The flask is equipped with a mechanical stirrer, a thermometer, a reflux condenser, and a nitrogen inlet. The nitrogen to be introduced is first run through two oxygen traps.

Nitrogen is bubbled into the ethylene glycol and KOH mixture for 20 minutes, and the temperature is then raised to 180° C.

1000 g of linoleic acid, corn oil, or safflower oil is then introduced into the flask. The mixture is heated at 180° C. under an inert atmosphere for 2.5 hours.

The reaction mixture is cooled to ambient conditions, and 600 ml HCL are added to the mixture which is stirred for 15 minutes. The pH of the mixture is adjusted to pH 3. Next, 200 ml of water is added into the mixture and stirred for 5 minutes. The mixture is transferred into a 4 L separatory funnel and extracted three times with 500 ml portions of hexane.

The aqueous layer is drained, and the combined hexane solution is extracted with four 250-ml portions of 5% NaCl solution.

The hexane is washed 3 times with water. The hexane is transferred to a flask, and the moisture in the hexane is removed with anhydrous sodium sulfate ($Na_2SO_4$). The hexane is filtered through Whatman paper into a clean 1000 ml round bottom flask, and the hexane is removed under vacuum with a rotoevaporator to obtain the CLA. The CLA is stored in a dark bottle under argon at −80° C. until time of use.

The CLA obtained by the practice of the described prior art methods of preparation typically contains two or more of the 9,11-octadecadienoic acids and/or 10–12-octadecadienoic acids and active isomers thereof. After alkali treatment, the compound may be in the free acid or salt form. The CLA is heat stable and can be used as is, or it may be dried and powdered. The CLA is readily converted into a non-toxic salt, such as the sodium or potassium salt, by reacting chemically equivalent amounts of the free acid with an alkali hydroxide at a pH of about 8 to 9.

Theoretically, eight (8) possible geometric isomers of 9,11 and 10,12-octadecadienoic acid (c9,c11; c9,t11; t9,c11; t9,t11; c10,c12; c10,t12; t10,c12; and t10,t12) would form from the isomerization of c9,c12 octadecadienoic acid. As a result of the isomerization, only four isomers (c9,c11; c9,t11; t10,c12; and c10,c12) would be expected. However, of the four isomers, c9,t11- and t10,c12- isomers are predominantly produced during the autoxidation or alkali isomerization of c9,c12-linoleic acid because of the co-planar characteristics of 5 carbon atoms around a conjugated double bond and spatial conflict of the resonance radical. The remaining two c,c-isomers are minor contributors.

The relatively higher distribution of the t,t-isomers of 9,11- or 10,12-octadecadienoic acid apparently results from the further stabilization of c9,t11- or t10,c12-geometric isomers, which is thermodynamically preferred, during an extended processing time or long aging period. Additionally, the t,t-isomer of 9,11- or 10,12-octadecadienoic acid predominantly formed during the isomerization of linoleic acid geometrical isomers (t9,t12-, c9,t12-, and t9,c12-octadecadienoic acid) may influence the final ratio of the isomers or the final CLA content in the samples.

Linoleic acid geometrical isomers also influence the distribution of minor contributors (c,c-isomers of 9,11- and 10,12-, t9,c11- and c11,t12-octadecadienoic acids). The 11,13-isomer might be produced as a minor product from c9,c12-octadecadienoic acid or from its isomeric forms during processing.

Conjugated linoleic acid (CLA) has long been of interest to biochemists and nutritionists. A recent article in INFORM, Vol. 7, No. 2, February 1996, published by the American Oil Chemists' Society summarizes some of the data developed so far. The article stresses the feed use for which the product is currently being developed, resulting in less fat and more lean meat in animals. A number of other recent articles stress effects in fighting cancer. In all cases, one isomer, 9(Z),11(E)-CLA, has been named as the active isomer, mainly because it alone is incorporated into the phospholipids of the organism being fed CLA.

CLA has been shown to have preventive effects on breast cancer in mice. CLA is not used for humans today, mostly because it is not available except in impure forms. CLA is not approved by the FDA, and impurities have a detrimental influence on toxicity tests to obtain FDA approval.

The problem with CLA, as it is available today, has been the fact that only a diverse mixture of isomers can be made. Conventional synthesis methods involve the isomerization of linoleic acid by potassium hydroxide at about 200° C. This procedure yields about equal amounts of the 9,11- and 10,12- isomers which are impossible to separate. The content of the preferred isomer of 9(Z),11(E)-CLA in the mix is about 20–30%. All of the isomers presumed to be in the mix have been synthesized but only by very laborious methods that are quite unsuitable for large scale manufacture.

Heating the linoleic acid in the presence of a base such as alkali, makes the double bond move over, and it does so in a haphazard way. The geometry changes, and the resultant product is the 9-cis, 11-trans isomer in a yield of only 23–40%.

It is an object of the present invention to provide a novel synthesis to provide over 50 per cent of the 9-cis, 11-trans octadecadienoic acid, also known as (9(Z),11(E)-octadecadienoic acid isomer.

It is an object of the present invention to provide a novel synthesis to provide over 70 per cent of the 9-cis, 11-trans octadecadienoic acid, also known as (9(Z),11(E)-octadecadienoic acid) isomer.

It is an object of the present invention to provide a higher purity 9-cis, 11-trans octadecadienoic acid than is available from conventional sources containing impurities which may have a detrimental influence on toxicity tests to obtain FDA approval.

It is an object of the present invention to provide a higher purity 9-cis, 11-trans octadecadienoic acid than is available from conventional sources containing diverse mixtures of isomers which have a detrimental influence on toxicity tests to obtain FDA approval.

These and other objects of the present invention will be described in the detailed description of the invention which follows. These and other objects of the present invention will become apparent to those skilled in the art from a careful review of the detailed description and from reference to the figures of the drawings.

SUMMARY OF THE INVENTION

The present invention provides a room temperature synthesis process for producing 9-cis, 11-trans octadecadienoic acid, including providing a tosylate of an ester of ricinoleic acid and 9-cis, 11-trans octadecadienoic acid formed when the tosylate reacts with diazabicyclo-undecene. In one aspect, the tosylate may be replaced by mesylate (methane sulfonate). The 9-cis, 11-trans octadecadienoic acid is formed in high yield. In one aspect, the tosylate of a methyl ester of ricinoleic acid is formed with tosyl chloride in a pyridine solvent. In one aspect, the tosylate is reacted with diazabicyclo-undecene in a polar, non-hydoxylic solvent acetonitrile.

DETAILED DESCRIPTION

Figure 1:
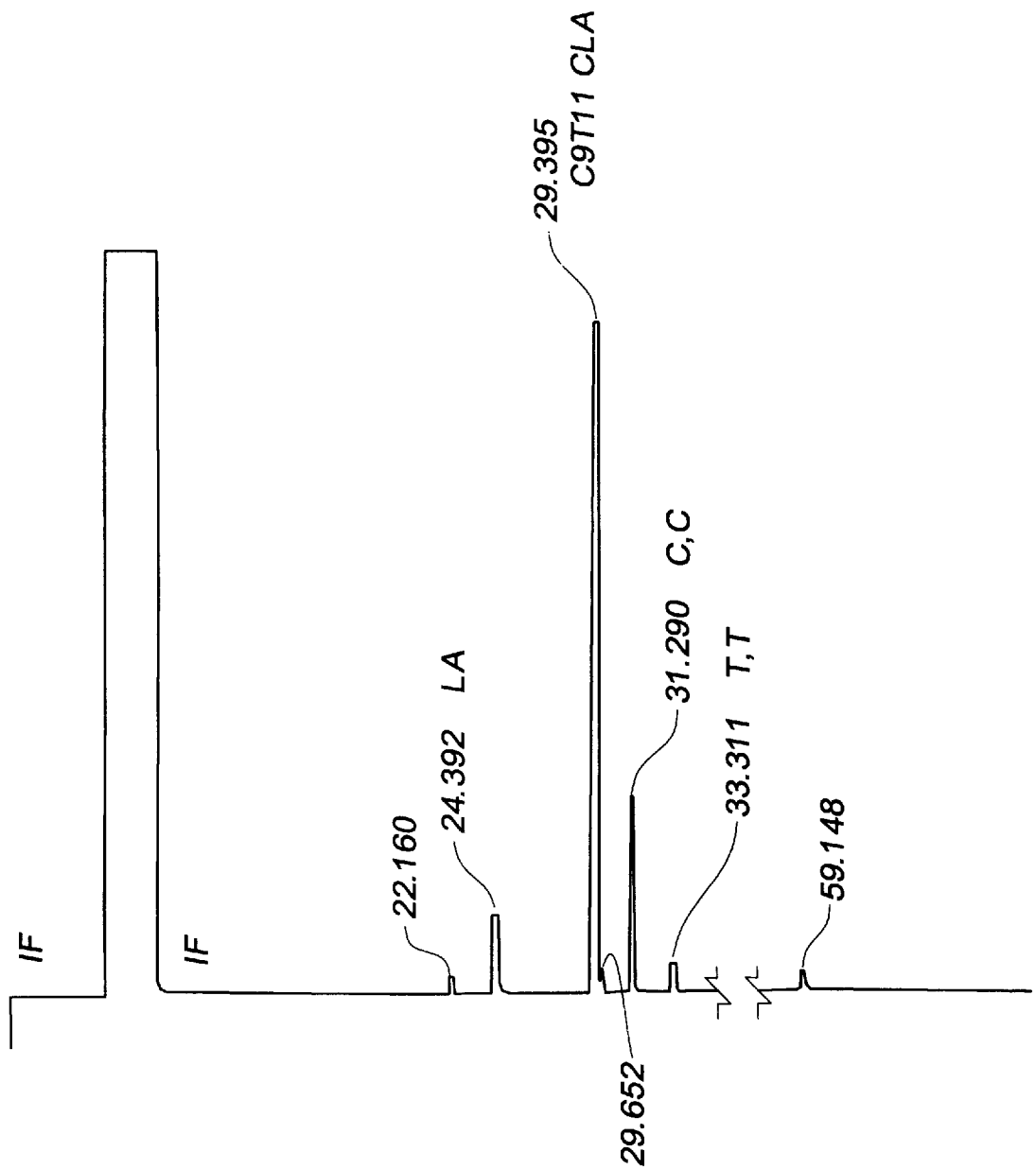
FIG. 1 is graphical view of a gas chromatography printout of the CLA produced by the process of the present invention.

The process of the present invention includes a novel method of synthesis to produce conjugated linoleic acid (CLA). In one aspect, the process of the present invention includes a novel method of synthesis for 9-cis, 11-trans octadecadienoic acid, also known as cis-9, trans-11 CLA; c9,t11 CLA; 9(Z),11(E)-octadecadienoic acid; or 9(Z),11(E) CLA.

The present invention produces octadecadienoic acid having 75%–79% or more of the isomer 9-cis, 11-trans octadecadienoic acid.

Another way of describing the present invention would be a novel synthesis to produce octadecadienoic acid having 75%–79% or more of the isomer 9(Z),11(E) octadecadienoic acid as the preferred isomer produced by the process of the present invention, but cis and trans will be used predominantly throughout the disclosure of the present invention.

My novel synthesis process can be summarized as follows in this detailed description of the process of the present invention.

I have found that a preparation of the preferred isomer of 9(Z),11(E)-CLA containing 75% of the desired isomer accompanied by the 9(Z),11(Z)-isomer can be made. From this material, the desired isomer can be separated by low temperature crystallization to give 90% and higher purity of the preferred isomer.

The following conditions are required for this novel synthesis reaction.

1. Methyl ricinoleate is made into the tosylate by reaction in pyridine as solvent. When other solvents are used and pyridine only as reagent, the reaction takes days and even then does not go to completion. I have found the reaction goes to completion overnight with pyridine as solvent at room temperature.

2. The tosylate is reacted with diazabicyclo-undecene (DBU) in acetonitrile as solvent (1 hour reflux) to give a clean complete reaction. Diazabicyclononene (DBN) is more expensive, but it also works. Solvents other than acetonitrile delay completion for many hours leading to side products and incomplete reactions. Other polar but non-hydoxylic solvents may also be useful. Examples of such other polar, non-hydoxylic solvents are dimethyl formamide, dimethyl sulfoxide, or chloroform. Care must be taken to remove traces of the pyridine from the previous step to avoid a substitution reaction. See Equations (3) and (4).

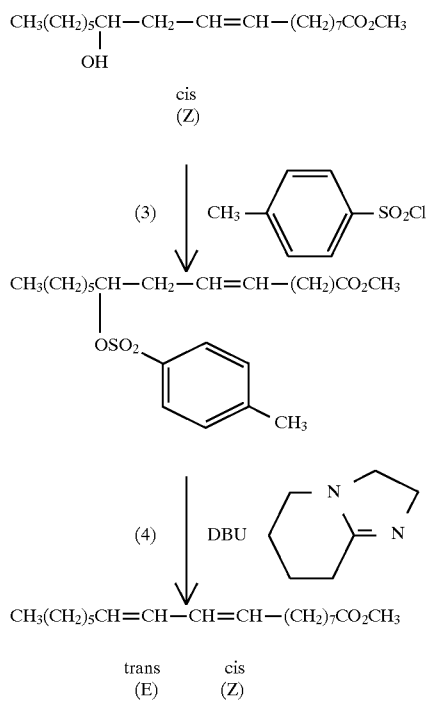

The novel synthesis of the present invention was performed in Example II.

EXAMPLE II 12 g (0.0384 mol) methyl ricinoleate were dissolved in 30 ml pyridine, and 10.5 g tosyl chloride were added. The mixture was left overnight at room temperature. An abundance of crystals were observed. 200 ml water and 150 ml hexane were added. The hexane layer was washed with 2×100 ml dilute acetic acid, 3×100 ml water, 1×100 ml brine, and then it was dried and evaporated: 16.8 g (100%) tosylate.

Dissolved in 70 ml acetonitrile, and 11.7 g (0.0768 mol) DBU (diazabicycloundecene) were added. After 3 hours at room temperature, 20–30% was reacted (TLC). After 15 hours, about 60% was reacted. Heated to 75–80° C. for 30 minutes, 90% reacted. After 2 hours at 75–80° C., all reacted and worked up. Poured into water, extracted with hexane (100 ml), washed with dilute acetic acid, water, and brine, evaporated: 9.0 g slightly yellow oil.

Repeated tosylate, worked up the same way, reacted with DBU as above for 11 days at approximately 12° C. All reacted from starting material. Gas Chromatography (GC) shows 78.51% 9(Z),11(E)-CLA and 17.14% 9(Z),11(Z)-CLA 10.36 g (91%) yield. Identifications of the isomers were confirmed by independent University analyses, using standards obtained from bacterial formation of CLA.

The gas chromatography printout from the product of Example II is shown in FIG. 1.

Example II shows the reaction of methyl ricinoleate tosylate with DBU in acetonitrile. In the first step, only tosyl chloride was used. It is preferred for the elimination purpose. Iodide can also be used. However, oxygen is excluded since traces of elemental iodine can isomerize double bonds which is undesirable in the process of the present invention. Methane sulfonyl chloride also can be used. In the first step, pyridine is preferred as solvent and as base to neutralize the HCl produced in the reaction. Other solvents work much less completely and much more slowly.

In the second step, DBN or DBU is essential. Other bases have not worked. Particularly important is the use of bases that cannot cause substitution. Sodium hydroxide has been used previously on the chloride, not the tosylate, but a mix of isomers results in which the trans, trans [9(E),11(E)] isomer was the only one isolated in pure form.

The preferred solvent for the second step is acetonitrile, although others, such as THF and toluene, also work but require higher temperatures and/or longer reaction times.

The mechanism is E2 elimination mechanism for the most part. Pure E2 would require exclusive formation of the 9(Z),11(E)-isomer. Finding 17% of the 9(Z),11(Z)-isomer shows that about 34% of the reaction forms at first a carbocation which equilibrates and leads to 17% 9(Z),11(Z)-isomer and 78% 9(Z),11(E)-isomer.

In accordance with the present invention, I have produced the cis-9, trans-11 isomer [9(Z),11(E)-isomer] an have verified independently that the main (78%) product is indeed the cis-9, trans-11 isomer [9(Z),11(E)-isomer], and that the minor (17%) product is the cis-9, cis-11-isomer [9(Z),11(E)-isomer]. Independent University analyses have identified these two peaks in gas chromatography (GC) traces. The independent University analyses used standards from bacterial produced CLA.

I also have found and shown a chemical proof.

Both compounds have two double bonds. I used a reaction which reduces one double bond at a time.

I then identified the three compounds with one double bond each and the compound with no more double bonds (stearic acid ester). The reaction was developed for unconjugated double bonds, and I have found it works as well with the conjugated double bonds.

Figure 2:
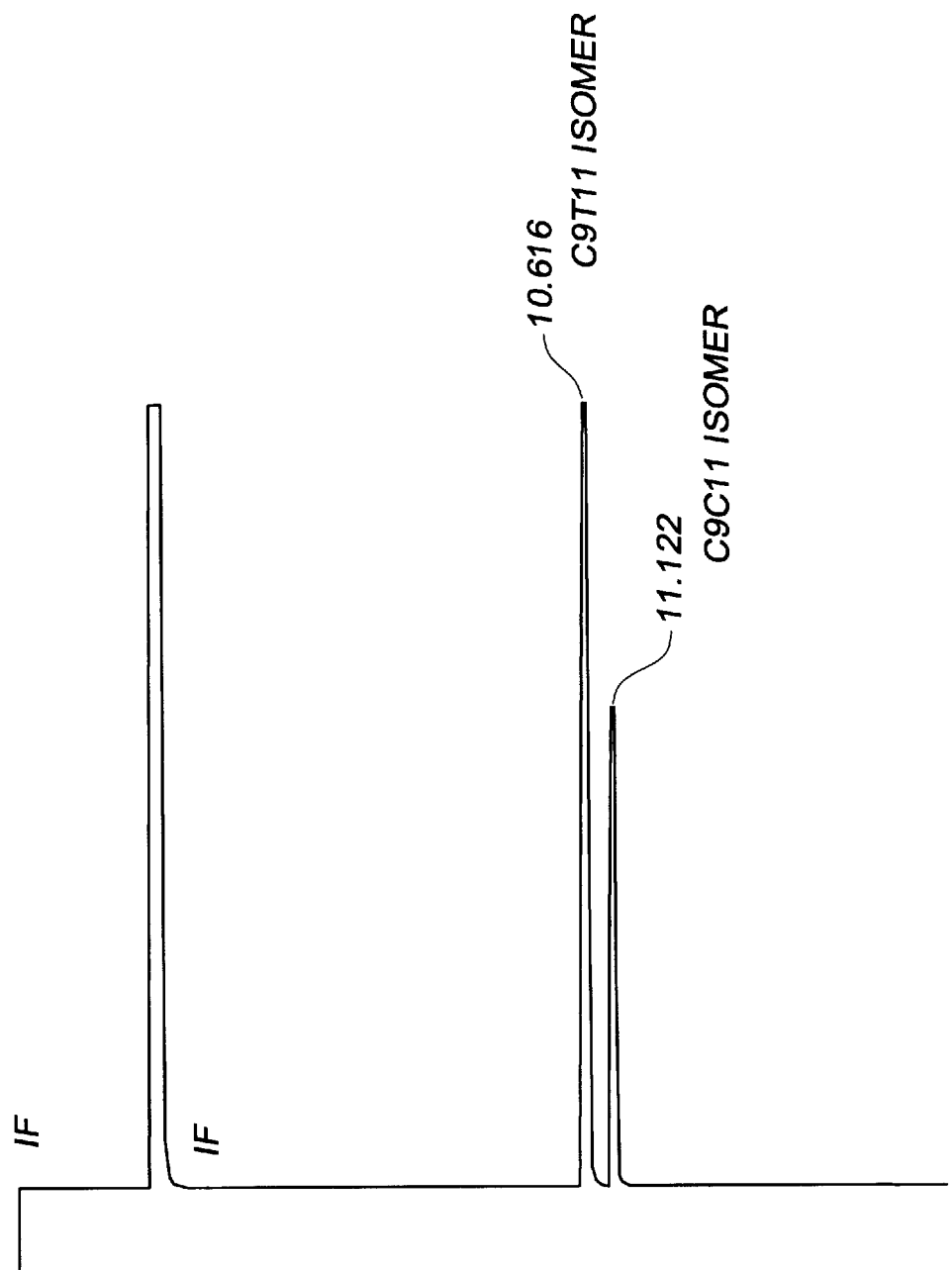
FIG. 2 is a graphical view of a gas chromatography printout of the starting material of the chemical analysis of the CLA produced by the process of the present invention.

FIG. 2 shows the starting material mixture (GC trace). The peak at 10.616 is the cis-9, trans-11 isomer. The smaller peak at 11.122 is the cis-9, cis-11 isomer. On reducing one double bond and then the other, the following reactions will take place.

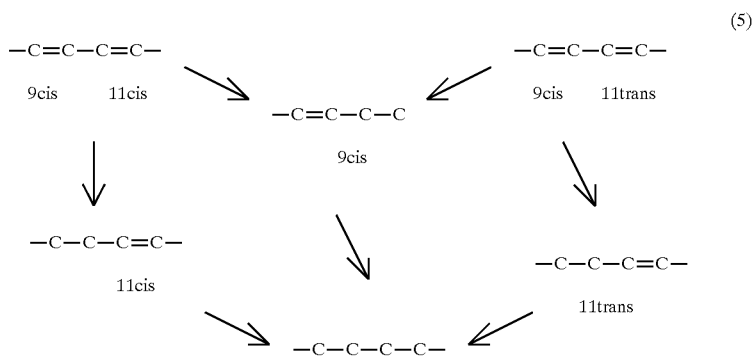

(5)

Hence as the reaction proceeds, twice as much cis-9 ester is formed as the others together, and since the starting material has five times as much cis-9, trans-11 than cis-9, cis-11, more trans-11 is formed than cis-11. Eventually, stearic ester predominates.

The chemical proof is performed and shown in Example III.

EXAMPLE III 550 mg of a CLA sample which by GC was 74% methyl 9(Z),11(E)-octadecadienoate and 25% methyl 9(Z),11(Z)-octadecadienoate were dissolved in 70 ml ethanol in a 250 ml three-neck flask equipped with thermometer and gas inlet and outlet tubes. A slow stream of oxygen was passed over the liquid which was heated to 40° C. with a heating mantle. One ml of 95% hydrazine was added and the temperature went to 45° C. and stayed there. Samples of 20 ml each were taken at 30 minutes and 60 minutes and the reaction stopped at 90 minutes. The samples were acidified with concentrated HCl and the solvents evaporated, 10 ml water added and extracted with 10 ml hexane. Hexane solutions were used for GC determinations.

Figure 3:
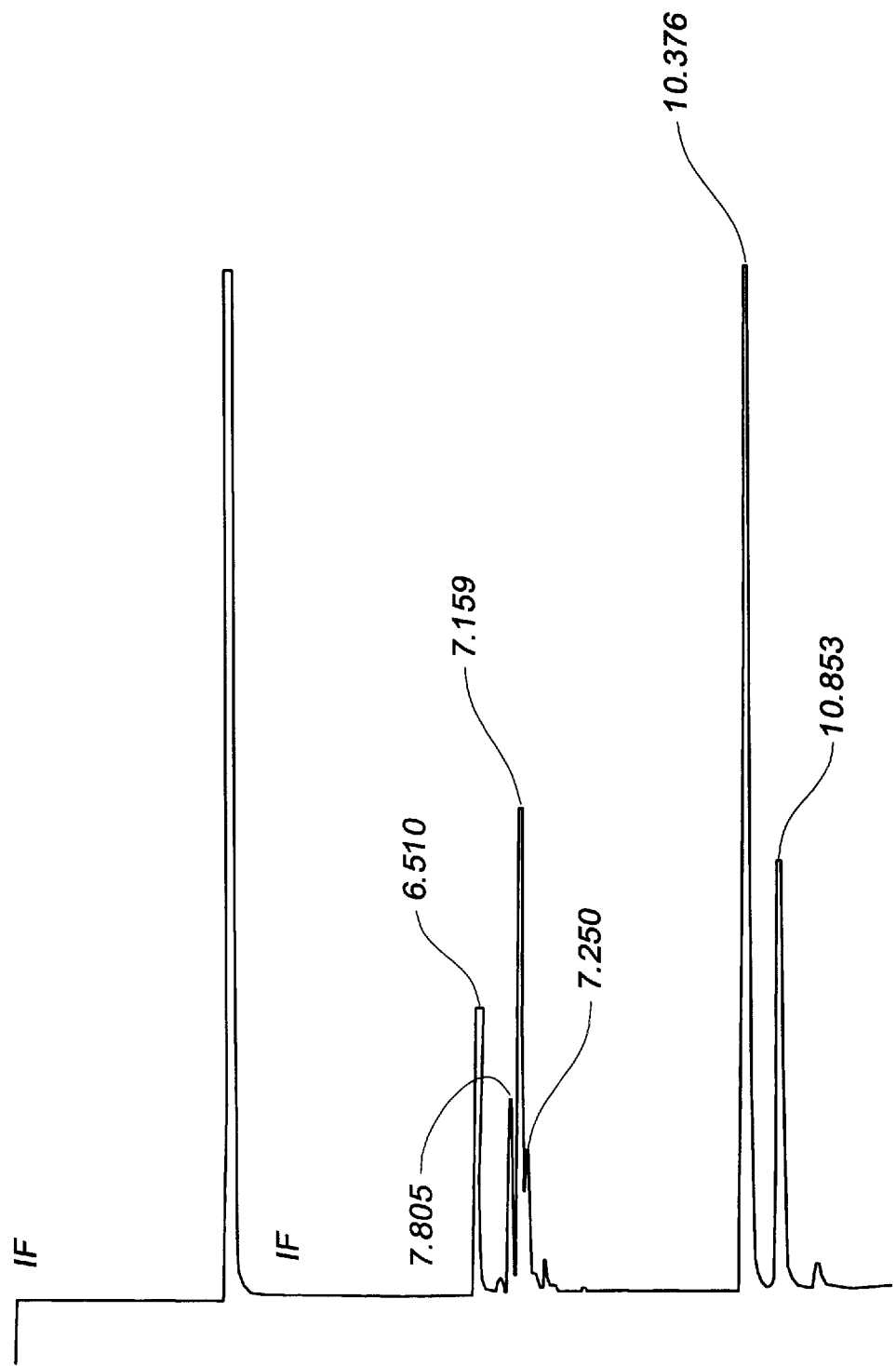
FIG. 3 is a graphical view of a gas chromatography printout at 30 minutes into the chemical analysis of the CLA produced by the process of the present invention.
Figure 4:
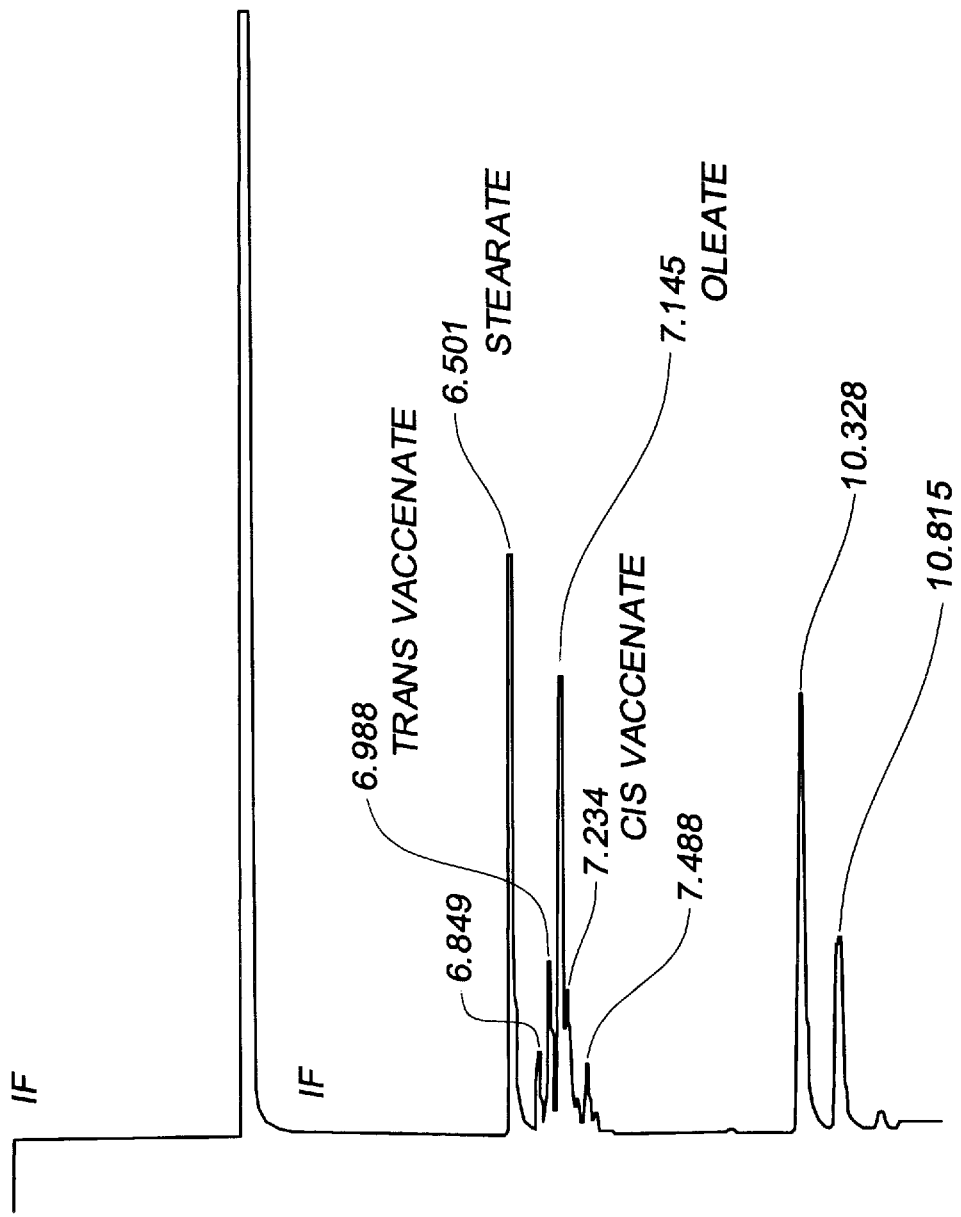
FIG. 4 is a graphical view of a gas chromatography printout at 60 minutes into the chemical analysis of the CLA produced by the process of the present invention.
Figure 5:
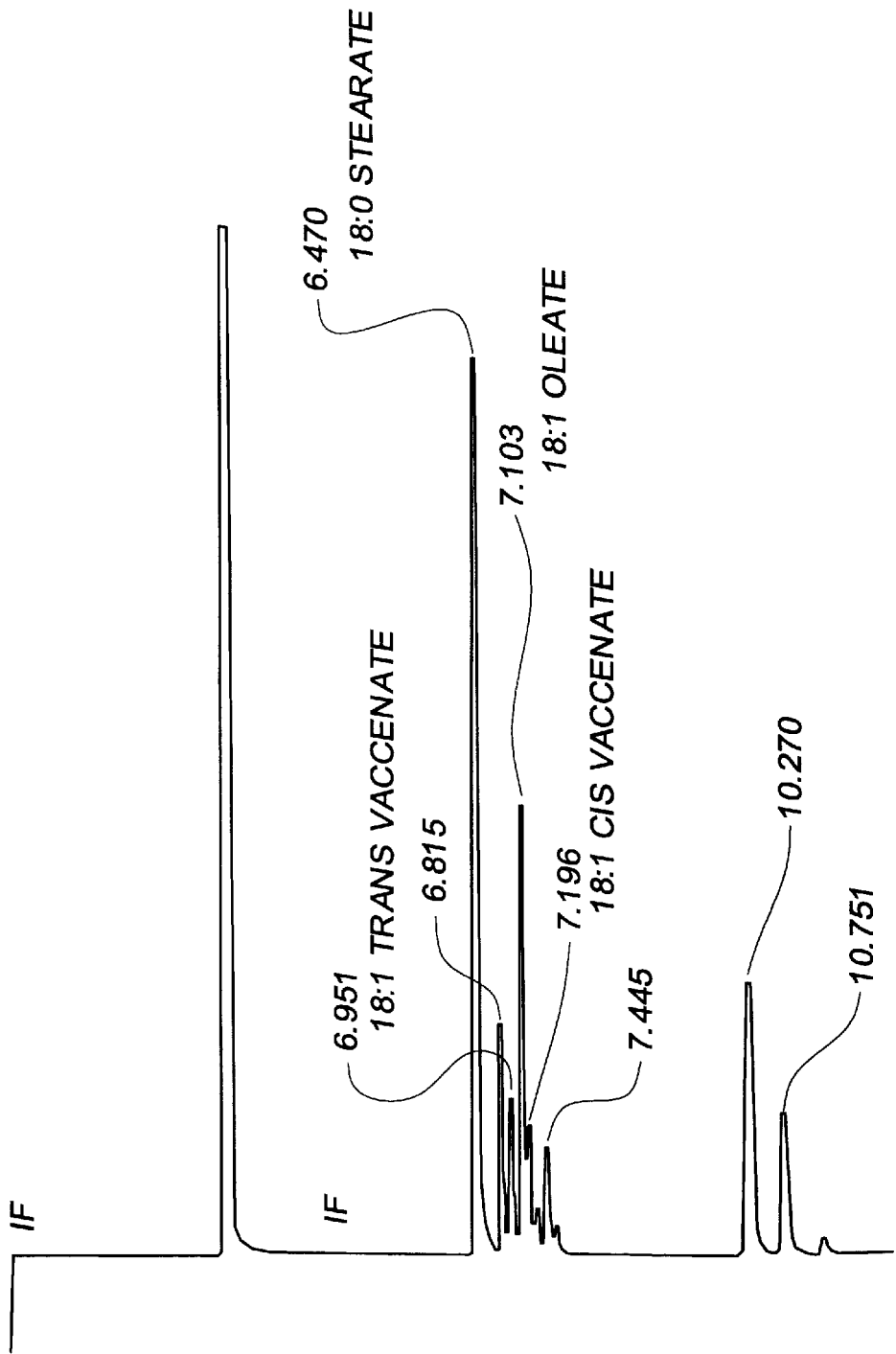
FIG. 5 is a graphical view of a gas chromatography printout at 90 minutes into the chemical analysis of the CLA produced by the process of the present invention.

FIG. 3 shows the reaction mixture after 30 minutes. Both starting materials are reduced in content, some stearic ester has been formed, and among the products, cis-9 (also called oleate) predominates. There is more trans-11 (also called trans vaccenate) than cis-11 (also called vaccenate). At 60 minutes (FIG. 4) and 90 minutes (FIG. 5), an analogous picture is seen; the starting materials are further diminished, and stearic ester becomes the biggest peak. For comparison, the traces for pure oleate, vaccenate, and bans vaccenate were run also. The GC technique does not always give absolute reproducibility, and hence pure compounds are done at the same time as the mixtures. The samples were run again on another column which pulled the peaks farther apart with similar results.

The present invention produces octadecadienoic acid not by cooking the linoleic acid in base, but by eliminating water from an ester of ricinoleic acid.

I have been able to recrystallize the product acid at low temperature from ethyl ether and petroleum ether. After three recrystallizations, a 97% pure sample results which melts at 19–20° C.

The recrystallized product purity can be verified by the method according to which the acid has been made in the prior art as described by the very laborious method of Gunstone and Russell (Chem. Soc., pp. 3782, 3787, 1955). These authors report a m.p. of 19–20.2° C.

A further development of my method avoids the use of pyridine and proceeds in one step from ricinoleate. Tosylation is done with p-toluenesulfonic anhydride, thereby avoiding any chloride in the mix which tends to produce substitution. The base is two moles of DBU. The solution contains the product and the salt of DBU and p-toluenesulfonic acid. This allows the easy regeneration of DBU and, if needed, that of p-toluenesulfonic acid. This reaction works well with castor oil itself. The product is a triglyceride with 90% CLA since castor oil is a triglyceride with 90% ricinoleic acid and 10% of a mix of oleic, linoleic, and the like acids.

Early work in the development of the novel synthesis of the present invention used methyl ricinoleate and phosphorylchloride yielded 12-chloro-ricinoleate. The 12-chloro-ricinoleate reacted with aqueous base or diazabicyclononene (DBN) yielded mixtures of CLA isomers. Accordingly, it was found that although phosphorylchloride was expected to be workable, it did not work. Chloride substitution of the hydroxyl was observed.

The reaction of the tosylate of methyl ricinoleate with reagents containing nucleophiles such as chloride ion, pyridine (or other nucleophilic amine) produced substitution rather than elimination.

Methyl ricinoleate reacted with Burgess' reagent, reputed to be a sure-fire reagent for splitting off water, showed no likely product by gas chromatography. Moreover, Burgess' reagent would be too expensive for a practical method.

The following actual examples describe the development of the novel synthesis of the present invention in detail.

EXAMPLE IV

A. 1 g of ricinoleic acid methyl ester was refluxed in 30 ml acetic acid with 3 ml acetic anhydride added and 1 g of Amberlyst-15 as catalyst for 3 hours. Poured into 200 ml water and stirred for 30 minutes. Picked up in ether, ether layer washed with water and dried and evaporated. TLC shows new spot where oleate shows positive impurities and some starting material.

B. 1 g of methyl ricinoleate was treated with 3 ml acetic anhydride in 10 ml pyridine overnight. Poured into water and extracted with ether. TLC shows single spot higher than starting material (the acetate of ricinoleate). Product was refluxed for 5 hours in 50 ml toluene with 1 g Amberlyst-15 as catalyst.

Evaporation after washing with water and adding of ether gave a clear oil with the same spot as A (cleaner reaction). Product of A+B was passed through silica column with hexane and "oleate" spot obtained pure: 800 ma. Gas chromatography showed bizarre mixture.

Amberlyst-15 is a sulfonic acid resin. Acid catalyzed splitting off of acetic acid from the acetate of ricinoleate produced complex mixtures.

EXAMPLE V

To 15.6 g (0.05 mol) of methyl ricinoleate and 5 g (0.06 mol) pyridine in 100 ml methylene chloride was added 9.5 g (0.05 mol) p-toluene sulfonyl chloride. The solution remained clear, and the next morning very little reaction was seen by TLC (ether:pet ether 30:70). After another 24 hours, very little more reaction. Added 10 ml triethyl amine and 4 g more toluene sulfonyl chloride. Left standing over the weekend. Very red solution, some solid. Washed with water, 2N HCl and 2×water. Dried and evaporated. Picked up in 200 ml hexane, and silica added till all the red color had been absorbed. Filtered and evaporated. TLC showed a little starting material, some almost at solvent front and most product a little ahead of starting material.

The 17 g product was dissolved in 100 ml methylene chloride and 7 g DBN (diazabicyclononene) added. After 12 hours, some increase in the top spot. After 5 days, about 50% was reacted. More DBN (2 g) was added and left standing for 2 weeks. Almost 90% top spot. Isolated by chromatography.

Tosylation with pyridine or triethylamine and tosyl chloride when heated leads to many side products because of substitution reactions of the amines with the intermediate tosylate.

Example V shows an attempt to split off toluene sulfonic acid to make CLA.

The Example shows a partially successful preparation of the tosylate of methyl ricinoleate. The reaction was slow and incomplete, use of inappropriate solvent. The reaction product was reacted with DBN (an analog of the later used DBU). The right product was formed but incompletely. Wrong solvent again.

The reaction to make the toluene sulfonate intermediate does not go well in solvents other than pure pyridine. The reaction to split off the toluene sulfonate does not go well except in acetonitrile.

It was tried to get the toluene sulfonate intermediate with triethyl amine in acetonitrile. Even after a week at room temperature, the reaction was not complete. Heating is not advised since the chloride ion present will lead to substitution by this ion.

EXAMPLE VI 15.6 g methyl ricinoleate (0.05 mol) were dissolved in 30 ml pyridine and with ice cooling. 7 g (0.046 mol) phosphorus oxychloride were added dropwise over 30 minutes. Left at room temperature for 24 hours and then heated at 55° C. for 1 hour. Poured into a mixture of 100 ml water and 100 ml methylene chloride. Organic layer washed with 2×200 ml 1N HCl and 3×100 ml water. Dried and filtered and evaporated. TLC shows fast moving spot which could be the CLA product and some starting material.

Example VI shows a reaction of methyl ricinoleate with phosphorus oxychloride and pyridine. The product was shown later by gas chromatography to be 12-chloro-analog of methyl ricinoleate. That product tended to form whenever chloride ions were present. Substitution is favored over the desired elimination. Heating the toluene sulfonate in pyridine with pyridine hydrochloride present produced only the 12-chloro compound.

EXAMPLE VII 1.3 g methyl ricinoleate was dissolved in 15 ml acetonitrile, heated to about 50° C., and 1 g of Burgess salt of methoxycarbonylsulfamoyl)-triethyl ammonium hydroxide was added (equimolar amount). Refluxed for one hour. Poured into water and extracted with methylene chloride. TLC (ether:pet ether 30:70) showed major spot almost at solvent front. GC showed no methyl linoleate.

Example VII shows an attempt to dehydrate methyl ricinoleate with Burgess' salt. The reaction with Burgess' salt worked partially, right solvent. But many side products were also formed and Burgess' salt is too expensive for a practical process.

This Example VII produced the desired CLA since it was later found that the CLA isomers do come out of the GC later than the unconjugated methyl linoleate. However, Burgess' salt is far too expensive to provide a practical procedure at $45.70 (1996) for 1 g.

EXAMPLE VIII

Methyl ricinoleate was prepared and converted to 12-chloro oleate by thionyl chloride.

Methyl 12-chloro oleate was treated with sodium hydroxide.

12-chloro compound was treated with DBN in methylene chloride over 3 days. The result was negative. The wrong spot gets bigger, but not by much.

Example VIII shows an attempt to split off HCl from methyl 12-chloro oleate. Methyl 12-chloro-oleate was prepared in an attempt to work with a chloro-group instead of the hydroxy group of the ricinoleate. Attempts to eliminate the chloro-group with DBN were unsuccessful. The TLC analytical technique does not distinguish well between the chloro- and the product compound. Also, reaction too slow.

The reaction of the chloro-compound with sodium hydroxide gives a mix like the prior art method.

EXAMPLE IX 10 g (0.032 mol) methyl ricinoleate were dissolved in 60 ml pyridine and 9.12 g (0.048 mol) tosyl chloride added. Left at room temperature overnight. TLC (E:PE 30:70) shows complete reaction (only spot at app. Rf=0.6). Refluxed for one hour. TLC shows complete reaction to spot at Rf=0.9. Worked up by treatment with water and hexane. Hexane layer washed with water, dried and evaporated: 6.4 g of oil, GC looks like 12-chloro compound.

Example IX shows a reaction of methyl ricinoleate with toluene sulfonyl (tosyl) chloride in pyridine and subsequent refluxing.

EXAMPLE X

Same run to make the tosylate but used 60 ml hexane and 10 ml pyridine. Needed to be warmed to effect solution. Overnight at room temperature showed only approximately 30% reaction by TLC. Evaporated down to pyridine (at approximately 40° C.) and 30 ml pyridine added. All converted to tosylate overnight at room temperature. Worked up and half refluxed in 20 ml pyridine for 40 minutes. Poured into pet ether and water. Some oil formed between pet ether layer and water layer, pyridinium salt, care had not been taken to remove all pyridine. Yield of ester with Rf=0.9 was 1.1 g.

The other half was dissolved in acetonitrile and 4 g (0.032 mol) DBN (diazabicyclononene) added. Left at room temperature over the weekend. All reacted. Some of the same insoluble oil formed. Yield of Rf=0.9 pet ether soluble oil: 2.0 g.

Example X shows (1) tosylate forms easily only in pyridine as solvent. Tosylate in acetonitrile with basic ion exchange resins have been tried without any success. Example X shows (2) whenever chloride ions are present, substitution by them is preferred. Example X shows (3) the presence of any pyridine causes substitution by pyridine yielding the pyridinium toluene sulfonate. Since DBN cannot substitute and an ester had formed which moved to the solvent front in TLC, the elimination of the elements of toluene sulfonic acid takes place, and the product was CLA.

Example X shows success in the first step. Tosylation is complete without side products when carried at room temperature in pyridine as solvent.

The elimination to form the desired product takes place on refluxing in pyridine. A lot of side product was observed. The easily separable pyridinium salt formed because of substitution of the tosyl group by pyridine.

EXAMPLE XI 5 g (0.016 mol) methyl ricinoleate was tosylated, worked up with dilute acetic acid (to remove all pyridine), water and brine. Dried and evaporated and dissolved in 50 ml tetrahydrofuran (THF) and 4 g DIPEA added. Left over the weekend: no reaction. Refluxed for 1 hour, no change. Cooled and 3.4 g DBN added. Left overnight at room temperature. Not much reacted. Refluxed for 4 hours: approximately 45% was reacted. Solvent evaporated and 20 ml acetonitrile added. Refluxed for 45 minutes. All converted (by TLC).

Example XI shows an attempt to do the elimination with a hindered base of diisopropylethylamine which cannot do a substitution like pyridine. No reaction was seen. With some DBN, some reaction was observed. A more polar solvent is needed, and the tetrahydrofuran was determined not to work. With acetonitrile, on heating, a complete reaction was quickly achieved. The products were submitted to gas chromatography, and the cat 75:20 ratio of product to side product with otherwise few side products was seen.

Example XI shows solvents other than acetonitrile do not work at room temperature. Organic bases other than DBN and DBU do not eliminate properly. DBU is less expensive but otherwise analogous to DBN.

DBN was used in toluene. It was done at reflux (120° C.) and then gave a CLA mixture. Thus, DBN or DBU use is essential for success. Use of acetonitrile as solvent is preferred by a large margin.

EXAMPLE XII 6.0 g of methyl ester of Example II was saponified with sodium hydroxide in methanol, overnight at room temperature. The acid was isolated by acidifying and extracting. It solidified at dry ice temperature but liquefied at 1 0° C. From it, 97% (GC) pure 9(Z),11(E)-isomer acid of m.p. 19–20° C. was isolated by recrystallizing in the dry ice chest, twice from pet ether and once from ethyl ether.

Example XII shows the preparation of the free acid from CLA methyl ester. Example XII shows the preparation of the free acid from the ester and the first recrystallization of the acid and proof that purity can be increased that way.

EXAMPLE XIII

The tosylate was prepared as in Example II, starting with 12 g methyl ricinoleate. The tosylate was dissolved in dimethyl sulfoxide (DMSO), 30 ml, and 11.7 g of diazabicyclo-undecene (DBU) was added.

After 7 hours, TLC (pet. ether: ethyl ether 70:30) showed approximately 40% completion; after 20 hours, approximately 60% done. Left at room temperature for 7 days: approximately 95% done; two layers had formed.

The product was not soluble in DMSO. The lower, DMSO, layer was yellow. The top layer was colorless.

Poured into 100 ml water and 100 ml hexane. The hexane layer was washed with 50 ml 1N HCl, 100 ml water and 100 ml brine. There was a small amount of yellow liquid between the layers which was also discarded.

The hexane layer was dried and evaporated: almost colorless oil, 9.6 g (84%). By gas chromatography, oil was 77.1% 9(Z),11(E)-CLA and 19.0% 9(Z),11(Z)-CLA.

Example XIII shows the elimination of toluene sulfonic acid from tosylated methyl ricinoleate in DMSO as solvent.

DMSO may be a less objectionable solvent than acetonitrile. Also, the separation of the product from the reaction mixture makes workup easier. The workup described in Example XIII with water and hexane is not be necessary for large scale runs.

EXAMPLE XIV

To a solution of 243.7 g (0.781 mol) of methyl ricinoleate in 900 ml acetonitrile was added dropwise over 2 hours a solution of 77 ml (114 g, 1 mol) of methane sulfonyl chloride in 192 ml acetonitrile. After 1 hour at room temperature, the resulting mixture was vacuum filtered, and most of the solvent was removed from the filtrate by vacuum evaporation. Water (300 ml) and a 50:50 mix of hexane and ethyl ether (300 ml) was added, and the upper layer was separated and washed with brine (2×200 ml). Dried with sodium sulfate and the solvents evaporated.

The same reaction was carried out with 257 g of methyl ricinoleate, and both batches were combined for vacuum distillation at 5 Torr: Fractions: (1) 33.3 g (2) 70.3 g (3) 212 g (4) 35.7 g.

Fractions (1), (2), and (3) came over at 173–174° C. Fraction (4) at 174–185° C. The content of fractions (1), (2), and (3) was the same: 75–77% 9(Z),11(E)-CLA, 15–17% 9(Z),11(Z)- CLA. Fraction (4) had appreciable amounts of 9(E),11(E)-CLA and was discarded. The total yield of acceptable product for fractions (1), (2), and (3) was 315.6 g (66%).

Example XIV shows methane sulfonyl group as the leaving group instead of the p-toluene sulfonyl group. With some changes in the procedure, including no pyridine as solvent in the first step, this method worked as well and gave a lesser yield of an almost identical product mix: 75–77% 9(Z),11(E)-CLA and 15–17% 9(Z) ,11(Z)-CLA.

The process of the present invention is a novel synthesis of conjugated linoleic acid (CLA). In one aspect, the process of the present invention includes a novel synthesis of a specific form of conjugated linoleic acid (CLA), a specific isomer of CLA. The specific isomer of the present invention is cis-9, trans-11 octadienoic acid.

There are a number of prior use patents on cis-9, trans-11 octadecadienoic acid. It is believed that the presumptive active ingredient is always cis-9, trans-11 octadecadienoic acid, but prior work has never achieved more than 40–45% pure sample.

The importance of my pure preparation is not only in the raising of lean animals but also in the potential as a cancer drug. Human trials not have been considered before a pure preparation was at hand.

The process of the present invention provides the first practical method for the preparation of 9(Z),11(E)-Octadecadienoic Acid or 9(Z),11(E)-CLA in high yield.

The process of the present invention produces the preferred isomer by splitting water off from ricinoleic acid. Elimination of water produces an (E)-double bond at the 11,12 position while keeping the 9,10(Z)-double bond of the ricinoleic acid.

Thus, it can be seen that the present invention accomplishes all of the stated objectives.

Although the invention has been illustrated by the preceding detailed description, it is not intended to be construed as being limited to the specific preferred embodiments employed therein.

Whereas particular embodiments of the invention have been described hereinabove, for purposes of illustration, it will be evident to those skilled in the art that numerous variations of the details may be made without departing from the invention as defined in the appended claims.

What is claimed is:

1. A synthesis process for producing 9-cis, 11-trans octadecadienoic acid, comprising:
    (a) providing a tosylate or mesylate of an ester of ricinoleic acid, wherein said tosylate or mesylate is formed by reacting an ester of ricinoleic acid with a tosyl chloride or a mesyl chloride; and
    (b) providing 9-cis, 11-trans octadecadienoic acid formed from said tosylate reacted with diazabicyclo-undecene, said 9-cis, 11-trans octadecadienoic acid having a purity greater than 50%.

2. A synthesis process as set forth in claim 1, wherein said providing a tosylate of an ester of ricinoleic acid comprises reacting a methyl ester of ricinoleic acid with tosyl chloride.

3. A synthesis process as set forth in claim 2, wherein said providing a tosylate of a methyl ester of ricinoleic acid comprises reacting said methyl ester of ricinoleic acid with tosyl chloride in a pyridine solvent.

4. A synthesis process as set forth in claim 1, wherein said tosylate reacted with diazabicyclo-undecene comprises tosylate reacted with diazabicyclo-undecene in a polar, non-hydoxylic solvent.

5. A synthesis process as set forth in claim 4, wherein said polar, non-hydoxylic solvent comprises acetonitrile.

6. A synthesis process as set forth in claim 1, wherein said 9-cis, 11-trans octadecadienoic acid formed from said tosylate reacted with diazabicyclo-undecene has a purity greater than 70%.

7. A synthesis process as set forth in claim 6, wherein diazabicyclononene is used in place of said diazabicyclo-undecene.

8. A synthesis process as set forth in claim 2, wherein said providing a tosylate of a methyl ester of ricinoleic acid comprises reacting said methyl ester of ricinoleic acid with tosyl chloride in an iodide solvent.

9. A synthesis process as set forth in claim 4, wherein said polar, non-hydoxylic solvent comprises THF or toluene.

10. A synthesis process as set forth in claim 1, wherein said providing a tosylate of an ester of ricinoleic acid comprises reacting a methyl ester of ricinoleic acid with p-toluene sulfonic anhydride.

11. A synthesis process as set forth in claim 1, wherein said providing a tosylate of an ester of ricinoleic acid comprises reacting a methyl ester of ricinoleic acid with methyl sulfonyl chloride.

12. A synthesis process for producing 9-cis, 11-trans octadecadienoic acid as set forth in claim 1, wherein said providing a tosylate of an ester of ricinoleic acid and said providing 9-cis, 11-trans octadecadienoic acid formed from said tosylate reacted with diazabicyclo-undecene are steps performed at room temperature.

13. A synthesis process as set forth in claim 4, wherein said polar, non-hydoxylic solvent comprises ethyl acetate or dimethyl sulfoxide.

14. A synthesis process as set forth in claim 1, wherein said providing a mesylate of an ester of ricinoleic acid comprises reacting a methyl ester of ricinoleic acid with mesyl chloride.

15. A synthesis process as set forth in claim 14, wherein said providing a mesylate of a methyl ester of ricinoleic acid comprises reacting said methyl ester of ricinoleic acid with mesyl chloride in acetonitrile and triethyl amine.

16. A synthesis process as set forth in claim 15, wherein said mesylate reacted with diazabicyclo-undecene comprises mesylate reacted with diazabicyclo-undecene in a polar, non-hydoxylic solvent.

17. A synthesis process for producing 9-cis, 11-trans octadecadienoic acid as set forth in claim 14, wherein said high yield is greater than 50%.

18. A synthesis process for producing 9-cis, 11-trans octadecadienoic acid as set forth in claim 17, wherein said high yield is greater than 70%.

19. A synthesis process for producing 9-cis, 11-trans octadecadienoic acid, comprising:
    (a) reacting a chloride selected from the group consisting of toluene sulfonyl, methane sulfonyl, and benzene sulfonyl with ricinoleic acid or an ester of ricinoleic acid at room tempera- ture in a first solvent to form an intermediate ester; and
    (b) reacting said intermediate ester with a compound selected from the group consisting of diazabicyclo-undecene and diazabicyclononene at room temperature in a second solvent of a compound selected form the group consisting of acetonitrile, toluene, tetrahydofuran, and dimethylsulfoxide to form 9-cis, 11-trans octadecadienoic acid in high yield.

20. A synthesis process for producing 9-cis, 11-trans octadecadienoic acid, comprising:
    (a) reacting tosyl chloride with methyl ester of ricinoleic acid at room temperature in a solvent of pyridine to form a tosylate; and
    (b) reacting said tosylate with diazabicyclo-undecene at room temperature in a solvent of acetonitrile to form 9-cis, 11-trans octadecadienoic acid in a yield higher than about 70%.

* * * * *